(12) United States Patent
Vanini et al.

(10) Patent No.: US 6,848,904 B1
(45) Date of Patent: Feb. 1, 2005

(54) SHADE GUIDE FOR EVALUATING THE OPTICAL APPEARANCE OF A DENTAL RESTORATION

(75) Inventors: Lorenzo Vanini, San Fedele Intelvi (IT); Eugenio Miceli, Genoa (IT); Thomas Niem, Korbach (DE)

(73) Assignees: Micerium SpA, Avegno (IT); GDF Gesellschaft fur Dentale Forschung und Innovationen GmbH, Rosbach (DE)

( * ) Notice: Subject to any disclaimer, the term of this patent is extended or adjusted under 35 U.S.C. 154(b) by 0 days.

(21) Appl. No.: 10/257,194

(22) PCT Filed: Apr. 12, 2000

(86) PCT No.: PCT/IB00/00453

§ 371 (c)(1), (2), (4) Date: Mar. 17, 2003

(87) PCT Pub. No.: WO01/76504

PCT Pub. Date: Oct. 18, 2001

(51) Int. Cl.$^7$ ............................................. A61C 19/10
(52) U.S. Cl. ............................. 433/26; 206/83; 356/421
(58) Field of Search ............................. 433/26, 203.1; 206/83; 356/421, 422

(56) References Cited

U.S. PATENT DOCUMENTS

| | | | |
|---|---|---|---|
| 4,541,801 A | * | 9/1985 | Mackert et al. ............... 433/26 |
| 4,810,193 A | | 3/1989 | Wieder |
| 5,078,598 A | | 1/1992 | Neisse |
| 5,149,267 A | | 9/1992 | Longhini et al. |
| 5,653,589 A | * | 8/1997 | Kleinmann .................. 433/26 |
| 5,725,372 A | * | 3/1998 | Leon .......................... 433/26 |

FOREIGN PATENT DOCUMENTS

| | | |
|---|---|---|
| DE | 297 02 486 U | 4/1997 |
| EP | 1 002 504 A | 5/2000 |

* cited by examiner

*Primary Examiner*—Todd E. Manahan
(74) *Attorney, Agent, or Firm*—Rankin, Hill, Porter & Clark

(57) ABSTRACT

The shade guide (1) consists of a colored polymerized composite material for evaluating the optical appearance of a dental restoration. The shade guide has a wedge-like shape and the composite material of which it is built up has a homogeneous structure. It has the advantage that it allows evaluation of the coloration of a dental restoration to be made with a curable composite material, particularly with a light curable composite material, before the restoration is performed.

29 Claims, 1 Drawing Sheet

SHADE GUIDE FOR EVALUATING THE OPTICAL APPEARANCE OF A DENTAL RESTORATION

Figure 1:
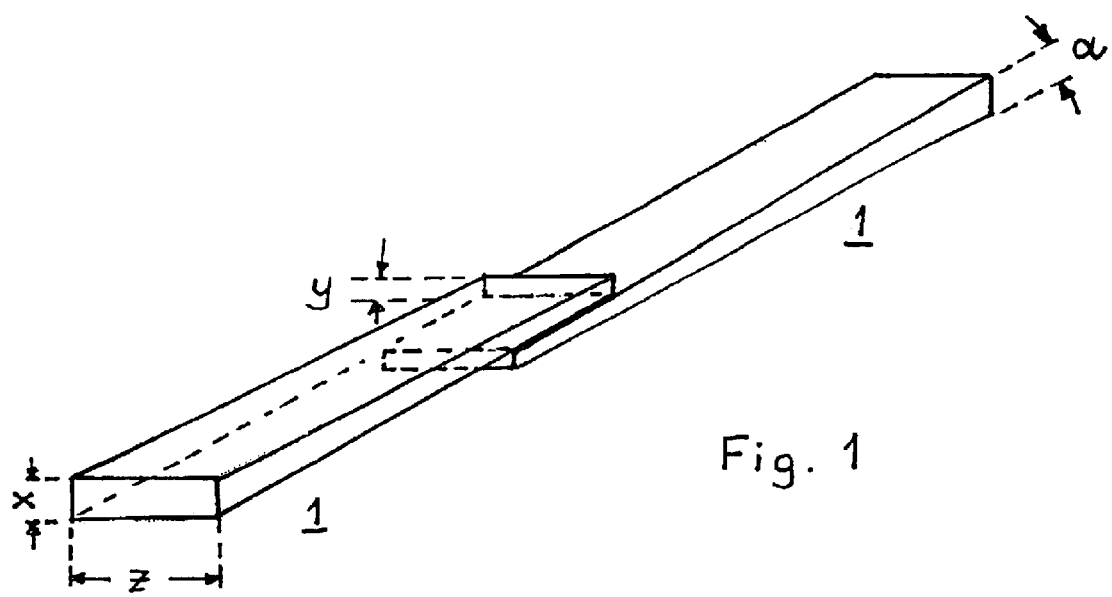

This invention relates to an assembly for dental restorations consisting of a curable dental composite material and a shade guide in accordance with the pre-characterising portion of claim 1 and a set of shade guides for use in such an assembly according to the preamble of claim 18.

Conventional shade guides are known in the form of fan type plates of uniform thickness usually made from pre-manufactured plastics which correspond more or less to the dental composite to be used. One major drawback of these prior art shade guides is their uniform thickness which allows no gradual superposition of the single guides.

Another known type of known shade guides consists of plastic (sleeves filled with the dental composite to be used and subsequently hardened. The drawback of these know guides is their inhomogenity caused by the different material for the sleeve (polyethylene or polypropylene) and for the hardened core (sophisticated polymethacrylates and other polymers).

Both types of know shade guides lead to significant colour deviations if used together with dental composite materials and in particular with light cured composites.

In U.S. Pat. No. 4,810,193 WIEDER a wedge-shaped shade guide is disclosed with a wedge angle of approx. 16° attached to a handle and which consists of a transparent plastic material. The relatively large wedge angle renders comparison of colours difficult. Furthermore comparison of colours is additionally impaired by the fact that the material of the shade guide and the material to be used as restoration material are not identical.

The invention as claimed aims at solving the above described problems.

The present invention provides an assembly as defined in claim 1 and a set of shade guides for use in such an assembly as defined in claim 18.

The assembly according to the invention has the advantage that it allows to evaluate the coloration of a dental restoration to be made with a curable composite material before the restoration is performed. To this effect the shade guides consist of the same but polymerised material as the curable dental composite material.

The homogenous wedge-like shaped shade guide has a wedge angle $\alpha$ in the range of 1 to 10°, preferably in the range of 1.5° to 5°. More preferably the wedge angle $\alpha$ is in the range of 1.8° to 3.5° and typically in the range of 2.0–3.0° which allows superposition of two or more shade guides of different colours over a relatively extended area of the shade guides.

The shade guide has the form of a frustum of a wedge.

The thickness x of the shade guide measured at its thickest end is in the range of 2.0 to 4.5 mm, preferably in the range of 2.5 to 3.5 mm. The thickness y of the shade guide measured at its thinnest end is in the range of 0.5 to 2,5 mm, preferably in the range of 0.8 to 1,5 mm.

The length of the shade guide is in the range of 10 to 60 mm, preferably in the range of 35 to 45 mm.

The width z of the shade guide is in the range of 4 to 10 mm, preferably in the range of 6.5 to 8.0 mm.

The composite material of the shade guides may be either chemically cured (two component material) or preferably light-cured. In the latter case either UV light or preferably light in the visible region can be used.

In order to prevent discoloration of the shade guides they should preferably comprise a colour stabiliser.

A number of further additives to the composite material of the shade guide may be used in order to reach maximum similarity to the dental restoration to be performed. Such additives may comprise fluorescent agents and opacifiers.

In a preferred embodiment of an assembly consisting of a curable dental composite material and a shade guide according to the invention the dental composite material comprises a first dentine-type composite material for the dentine part of a tooth and a second enamel-type composite material for the enamel part of a tooth in order to copy as truly as possibly the natural dental structure and coloration.

The system can be further elaborated by using

A) a first set of $n \geq 2$ shade guides consisting of the same but polymerised material as the dentine-type composite material; and
B) a second set of $n \geq 2$ shade guides consisting of the same but polymerised material as the enamel-type composite material.

The number n is chosen from the group of the integers 3, 9, 21, 23 or 26 and is preferably in the range of 4 to 30, typically in the range of 10 to 25.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

In the drawings:

FIG. 1 is a perspective view of two partially superimposed shade guides according to the invention.

FIG. 1 shows a shade guide 1 for evaluating the optical appearance of a dental restoration having the form of a frustum of a wedge and consisting of a homogenous coloured polymerised composite material. The composite material is light-cured so as to match as truly as possible the colour of the light curable dental composite material to be used for the dental restoration.

The shade guide consists of the same but polymerised material as the light curable dental composite material.

The angle of the wedge of the frustum of a wedge is 2.5°.

The length of the frustum is 40 mm and its width is 7.2 mm. The thickness x of the shade guide measured at its thickest end is 3 mm the thickness y of the shade guide measured at its thinnest end is 1.1 mm.

As shown in FIG. 1 an anterior shade guide 1 is partially superimposed with an posterior shade guide having a different colour in order to give an indication of the colour to be obtained by mixing two components corresponding to two shade guides of different colour.

By using a system of different shade guides and of corresponding composite material a large variety of possible colour combination can be evaluated before performing the dental restoration.

What is claimed is:

1. A shade guide consisting of a colored polymerized composite material for evaluating an optical appearance of a dental restoration and having a wedge-like shape, wherein:
   a wedge angle $\alpha$ of the shade guide (1) is in the range of 1 to 10°; and
   the composite material has a homogenous structure.

2. The shade guide according to claim 1, wherein the wedge angle $\alpha$ is between about 1.5° to 5°.

3. The shade guide according to claim 2, wherein the wedge angle $\alpha$ is between about 1.8° to 3.5°.

4. The shade guide according to claim 1, wherein the shade guide is formed as a frustum of a wedge.

5. The shade guide according to claim 1, wherein a thickness (x) of the shade guide measured at its thickest end is between about 2.0 to 4.5 mm.

6. The shade guide according to claim 1, wherein a thickness (y) of the shade guide measured at its thinnest end is between about 0.5 to 2.5 mm.

7. The shade guide according to claim 1, wherein a length of the shade guide is between about 10 to 60 mm.

8. The assembly according to claim 1, wherein a width (z) of the shade guide is between about 4 to 10 mm.

9. The shade guide according to claim 1, wherein the composite material is chemically cured.

10. The shade guide according to claim 1, wherein the composite material is light-cured.

11. The shade guide according to claim 10, wherein the composite material is light-cured with light in the visible region.

12. The shade guide according to claim 1, wherein the composite material comprises a color stabilizer.

13. The shade guide according to claim 1, wherein the composite material comprises a fluorescent agent.

14. The shade guide according to claim 1, wherein the composite material comprises an opacifier.

15. An assembly for dental restorations comprising a curable dental composite material and shade guides according to claim 1, wherein the shade guides consist of the same but polymerized material as the curable dental composite material.

16. The assembly according to claim 15, wherein the dental composite material is a two component chemically-curable composite.

17. The assembly according to claim 15, wherein the dental composite material is a light-curable composite.

18. The assembly according to claim 15, wherein the dental composite material comprises a first dentine-type composite material for the dentine part of a tooth and a second enamel-type composite material for the enamel part of a tooth.

19. The assembly according to claim 18, further comprising:

A) a first set of n≧2 shade guides consisting of the same but polymerized material as the dentine-type composite material; and, B) a second set of n≧2 shade guides consisting of the same but polymerized material as the enamel-type composite material.

20. The assembly according claim 19, wherein the number n is chosen from the group of the integers 3, 9, 21, 23 or 26.

21. The assembly according to claim 19, wherein the number n is between about 4 to 30.

22. The assembly according to claim 19, wherein the number n is between about 10 to 25.

23. A set of at least n≧2 shade guides (1) according to claim 1, wherein the shade guides (1) have different colors.

24. The shade guide according to claim 2, wherein the wedge angle α is between about 2.0 to 3.0°.

25. The shade guide according to claim 1, wherein a thickness (x) of the shade guide measured at its thickest end is between about 2.5 to 3.5 mm.

26. The shade guide according to claim 1, wherein a thickness (y) of the shade guide measured at its thinnest end is between about 0.8 to 1.5 mm.

27. The shade guide according to claim 1, wherein a length of the shade guide is between about 35 to 45 mm.

28. The shade guide according to claim 1, wherein a width (z) of the shade guide is between about 6.5 to 8.0 mm.

29. The shade guide according to claim 1 having a continuously tapering wedge-like shape.

* * * * *